US 8,632,564 B2

(12) United States Patent
Cunningham (10) Patent No.: US 8,632,564 B2
(45) Date of Patent: Jan. 21, 2014

(54) APPARATUS, SYSTEM, AND METHOD FOR PERFORMING AN ELECTROSURGICAL PROCEDURE

(75) Inventor: James S. Cunningham, Boulder, CO (US)

(73) Assignee: Covidien LP, Mansfield, MA (US)

( * ) Notice: Subject to any disclaimer, the term of this patent is extended or adjusted under 35 U.S.C. 154(b) by 908 days.

(21) Appl. No.: 12/353,470

(22) Filed: Jan. 14, 2009

(65) Prior Publication Data

US 2010/0179546 A1 Jul. 15, 2010

(51) Int. Cl.
*A61B 17/00* (2006.01)
*A61B 18/18* (2006.01)

(52) U.S. Cl.
USPC ............................................. 606/207; 606/50

(58) Field of Classification Search
USPC ................. 606/32, 45, 50–52, 205–211
See application file for complete search history.

(56) References Cited

U.S. PATENT DOCUMENTS

| | | | |
|---|---|---|---|
| 5,403,342 A | | 4/1995 | Tovey et al. |
| 5,693,051 A | * | 12/1997 | Schulze et al. ................. 606/51 |
| 5,810,764 A | | 9/1998 | Eggers et al. |
| 6,248,124 B1 | | 6/2001 | Pedros et al. |
| 6,533,784 B2 | | 3/2003 | Truckai et al. |
| 6,569,105 B1 | | 5/2003 | Kortenbach et al. |
| 7,101,371 B2 | | 9/2006 | Dycus et al. |
| 7,179,255 B2 | | 2/2007 | Lettice et al. |
| 7,270,664 B2 | | 9/2007 | Johnson et al. |
| 7,318,823 B2 | | 1/2008 | Sharps et al. |
| 7,384,420 B2 | * | 6/2008 | Dycus et al. ................... 606/51 |
| 2003/0171747 A1 | | 9/2003 | Kanehira et al. |
| 2003/0229344 A1 | * | 12/2003 | Dycus et al. ................... 606/51 |
| 2004/0078035 A1 | | 4/2004 | Kanehira et al. |
| 2009/0177094 A1 | * | 7/2009 | Brown et al. ................ 600/476 |

FOREIGN PATENT DOCUMENTS

| | | |
|---|---|---|
| CA | 2104423 | 2/1994 |
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |

(Continued)

OTHER PUBLICATIONS

U.S. Appl. No. 12/336,970, filed Dec. 17, 2008.

(Continued)

*Primary Examiner* — Theodore Stigell
*Assistant Examiner* — Rebecca E Eisenberg (57) ABSTRACT

An electrosurgical forceps adapted to connect to an electrosurgical energy source is provided. The electrosurgical forceps includes a housing having a shaft that extends therefrom that defines a longitudinal axis therethrough. The electrosurgical forceps includes an end effector assembly operatively connected to a distal end of the shaft and includes a pair of first and second jaw members. One or both of the jaw members being partially manufactured from a shape memory alloy (SMA). Each of the first and second jaw members adapted to connect to a heat source and an electrical electrosurgical energy source. One or both of the jaw members is movable relative to the other from a normally open spaced configuration to a closed configuration upon transition of the SMA from a martensite phase to an austenite phase as a result of selectively supplying heat from the heat source thereto.

9 Claims, 4 Drawing Sheets

(56) References Cited

FOREIGN PATENT DOCUMENTS

| | | |
|---|---|---|
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO03101311 | 12/2003 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Jan. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.

(56) References Cited

OTHER PUBLICATIONS

Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

\* cited by examiner

APPARATUS, SYSTEM, AND METHOD FOR PERFORMING AN ELECTROSURGICAL PROCEDURE

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an electrosurgical apparatus that includes an end effector assembly configured for use with various size access ports.

2. Description of Related Art

Electrosurgical apparatuses (e.g., electrosurgical forceps) are well known in the medical ails and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) and laparoscopic apparatus for remotely accessing organs through smaller, puncture-like incisions or natural orifices. As a direct result thereof patients tend to benefit from less scarring and reduced healing time. Typically, the forceps are inserted into the patient through one or more various types of cannulas or access ports (typically having an opening that ranges from about five millimeters to about twelve millimeters) that has been made with a trocar; as can be appreciated, smaller cannulas are usually preferred.

Forceps that are configured for use with small cannulas (e.g., cannulas less than five millimeters) may present design challenges for a manufacturer of electrosurgical instruments.

SUMMARY

As noted above, smaller cannulas or access ports are usually preferred during an endoscopic or laparoscopic procedure. However, because of size constraints of the cannula or access port, endoscopic forceps that are configured for use with smaller cannulas may present design challenges for a manufacturer (e.g., designing an end effector assembly of an endoscopic forceps without compromising the integrity and/or functionality thereof).

Therefore, it may prove useful in the relevant arts to provide an electrosurgical forceps that includes an end effector assembly that is configured for use with various types of cannulas or access ports including those that are less than five millimeters. With this purpose in mind, the present disclosure provides an electrosurgical forceps adapted to connect to an electrosurgical energy source for performing an electrosurgical procedure. The electrosurgical forceps includes a housing having a shaft that extends therefrom that defines a longitudinal axis therethrough. An end effector assembly operatively connects to a distal end of the shaft and includes a pair of first and second jaw members one of which is partially manufactured from a shape memory alloy (SMA). Each of the first and second jaw members are adapted to connect to a heat source and an electrical electrosurgical energy source. One of the jaw members is movable relative to the other from a normally open configuration to a closed configuration upon transition of the SMA from a martensite phase to an austenite phase as a result of selectively supplying heat from the heat source thereto.

The present disclosure also provides a method for performing an electrosurgical procedure. The method includes the initial step of providing a bipolar forceps adapted to connect to an electrosurgical energy source for performing an electrosurgical procedure. The bipolar forceps includes a housing having a shaft that extends therefrom that defines a longitudinal axis therethrough. An end effector assembly operatively connects to a distal end of the shaft and includes a pair of first and second jaw members one which being partially manufactured from a shape memory alloy (SMA). Each of the first and second jaw members adapted to connect to a heat source and an electrical electrosurgical energy source. One of the jaw members is movable relative to the other from a normally open spaced configuration to a closed configuration upon transition of the SMA from a martensite phase to an austenite phase as a result of selectively supplying heat from the heat source thereto. The method includes the steps of: activating the heat source causing at least one of the jaw members to move towards the other such that tissue is grasped therebetween; and applying electrosurgical energy to the jaw members such that a tissue seal may be effected therebetween.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, it is to be understood that the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes an end effector assembly having a jaw assembly that includes a pair of jaw members in operative communication with a source of electrosurgical energy that is in operative communication with or includes a control system One or both of the jaw members are made from memory alloy metal and heat-activated.

Figure 1:
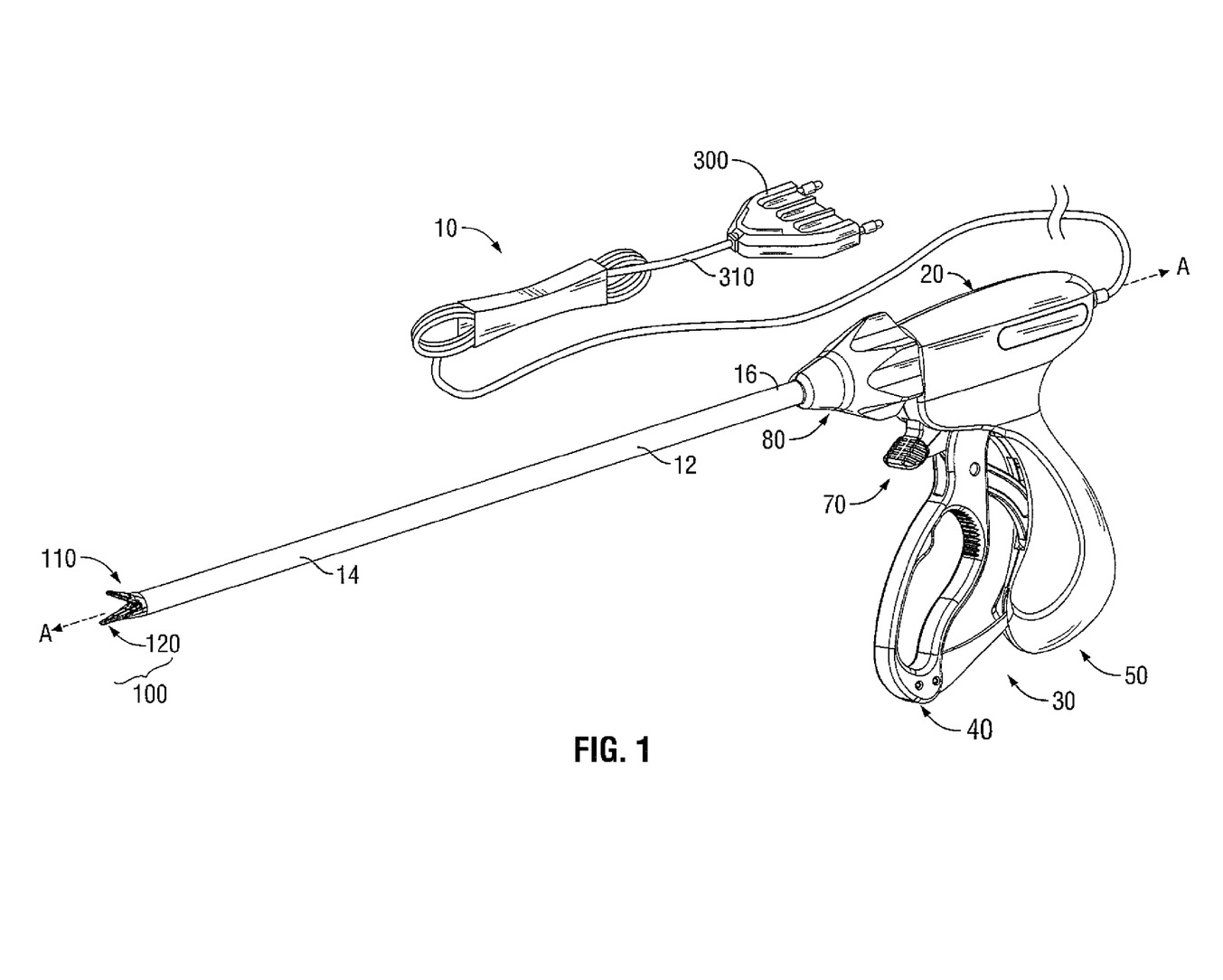
FIG. 1 is a perspective view of a bipolar forceps including an end effector assembly, an electrosurgical generator including a control system, and a fluid source according to an embodiment of the present disclosure.

With reference to FIG. 1, an illustrative embodiment of an electrosurgical apparatus (e.g., bipolar forceps 10) for performing an electrosurgical procedure is shown. Bipolar forceps 10 is operatively and selectively coupled to an electrosurgical generator (generator 200) for performing an electrosurgical procedure. As noted above, an electrosurgical procedure may include sealing, cutting, cauterizing coagulating, desiccating, and fulgurating tissue; all of which may employ RF energy. Generator 200 may be configured for monopolar and/or bipolar modes of operation. Generator 200 may include or is in operative communication with a system (system 300) that may include one or more processors in operative communication with one or more control modules that are executable on the processor. A control module (not explicitly shown) instructs one or more modules to transmit electrosurgical energy, which may be in the form of a wave or signal/pulse, via one or more cables (e.g., a cable 410) to one or both of the seal plates 118, 128. For a more detailed description of the generator 200 and/or system 300 reference is made to commonly owned U.S. application Ser. No. 10/427,832.

With continued reference to FIG. 1, the electrosurgical apparatus can be any suitable type of electrosurgical apparatus, including but not limited to electrosurgical apparatuses that can grasp and/or perform any of the above mentioned electrosurgical procedures. As noted above, one type of electrosurgical apparatus may include bipolar forceps 10 as disclosed in United States Patent Publication No. 2007/0173814 entitled "Vessel Sealer and Divider For Large Tissue Structures". A brief discussion of bipolar forceps 10 and components, parts, and members associated therewith is included herein to provide further detail and to aid in the understanding of the present disclosure.

Bipolar forceps 10 is shown for use with various electrosurgical procedures and generally includes a housing 20, a handle assembly 30 that includes a movable handle 40 and a fixed handle 50, a rotating assembly 80, a push button assembly 60, a trigger assembly 70, a shaft 12, and an end effector assembly 100, which mutually cooperate to grasp, seal and divide large tubular vessels and large vascular tissues. Although the majority of the figure drawings depict a bipolar forceps 10 for use in connection with endoscopic surgical procedures, the present disclosure may be used for more traditional open surgical procedures or laparoscopic procedures.

Shaft 12 has a distal end 16 dimensioned to mechanically engage the end effector assembly 100 and a proximal end 14 that mechanically engages the housing 20. In the drawings and in the descriptions which follow, the term "proximal," as is traditional, will refer to the end of the forceps 10 that is closer to the user, while the term "distal" will refer to the end that is farther from the user.

The distal end 16 may include one or more structures 250 (see FIG. 3A, for example) that is/are configured to support each of the jaw members 110, 120 of end effector assembly 100. The distal end 16 of shaft 12 may be configured to allow the jaw members 110, 120 to move from an open position, wherein the jaw members 110, 120 are disposed in spaced relation relative to one another, to a clamping or closed position, wherein the jaw members 110, 120 cooperate to grasp tissue therebetween.

Figure 2:
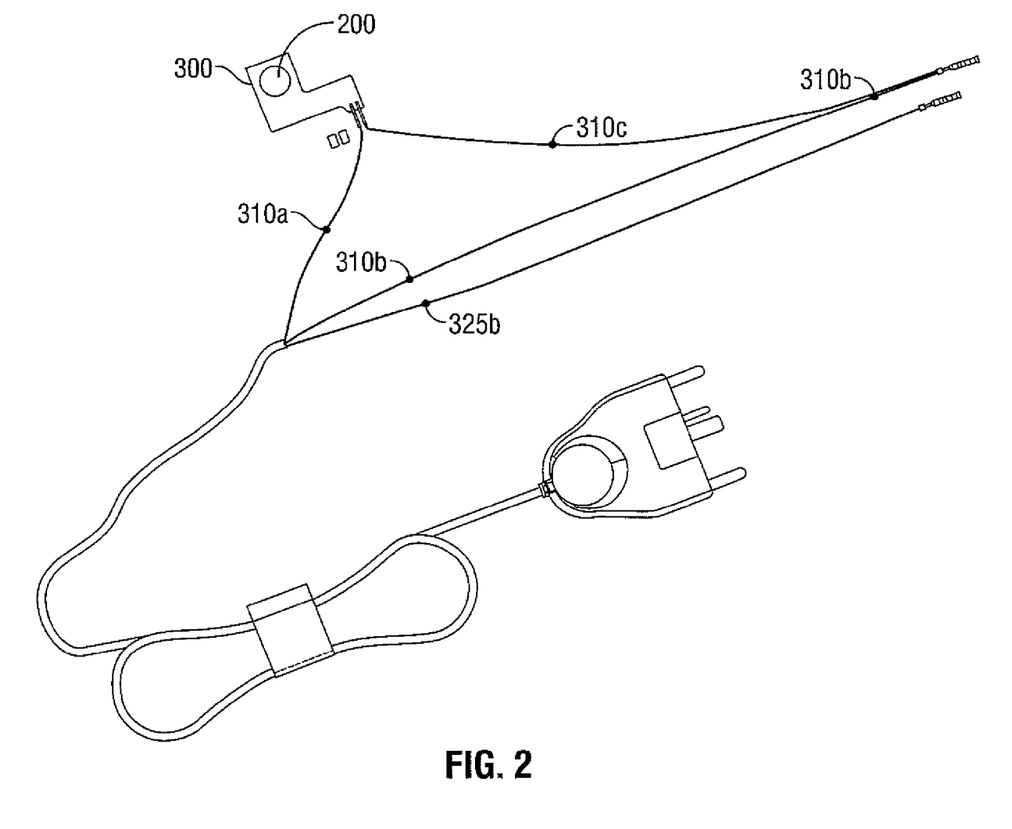
FIG. 2 is a schematic representation of an electrical configuration for connecting the bipolar forceps to the electrosurgical generator depicted in FIG. 1.

Forceps 10 includes an electrosurgical cable 410 that connects the forceps 10 to a source of electrosurgical energy, e.g., generator 200, shown schematically in FIG. 2. As shown in FIG. 2, cable 410 is internally divided into cable leads 410a, 410b, 410c, and 425b which are designed to transmit electrical potentials through their respective feed paths through the forceps 10 to the end effector assembly 100.

For a more detailed description of shaft 12, handle assembly 30, push button assembly 60, trigger assembly 70, rotating assembly 80 and electrosurgical cable 410 (including line-feed configurations and/or connections) reference is made to commonly owned Patent Publication No., 2003-0229344, filed on Feb. 20, 2003, entitled VESSEL SEALER AND DIVIDER AND METHOD OF MANUFACTURING THE SAME.

With reference again to FIG. 1, bipolar forceps 10 operatively couples to generator 200 such that jaw members 110, 120 may be heat activated. End effector assembly 100 is shown attached at the distal end 16 of shaft 12 and includes the pair of opposing jaw members 110 and 120.

Jaw member 110 includes an insulative jaw housing 117 and an electrically conductive seal plate 118 (seal plate 118). Insulator 117 is configured to securely engage the electrically conductive seal plate 118. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118. In embodiments, jaw housing 117 is made from a malleable, heat resistant material such that jaw housing 117 may flex or bend upon application of heat to jaw member 110 and/or seal plate 118. That is, because the jaw members 110, 120, or members associated therewith (e.g., seal plates 118, 128), are configured to move from opened to closed positions upon the application of heat thereto, so too should the jaw housings 117, 127.

Jaw member 120 includes a similar structure having an outer insulative housing 127 that is overmolded to capture seal plate 128 and configured to function as described hereinabove with regard to insulative housing 117.

Figure 3A:
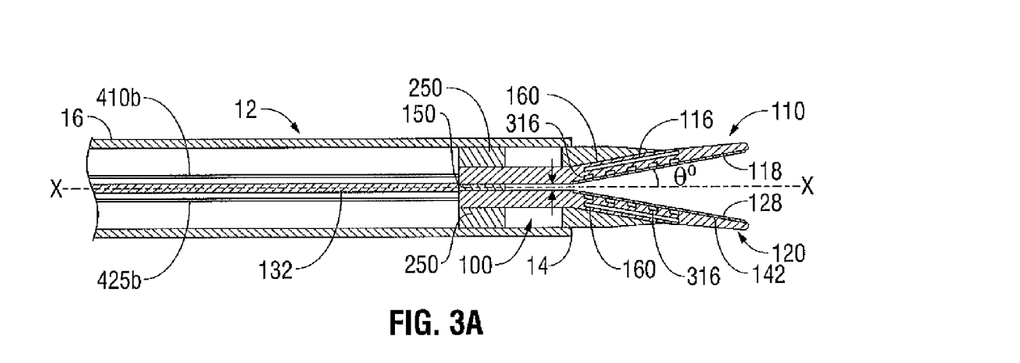
FIGS. 3A-3C are enlarged, side views of the end effector assembly of FIG. 1.
Figure 3B:
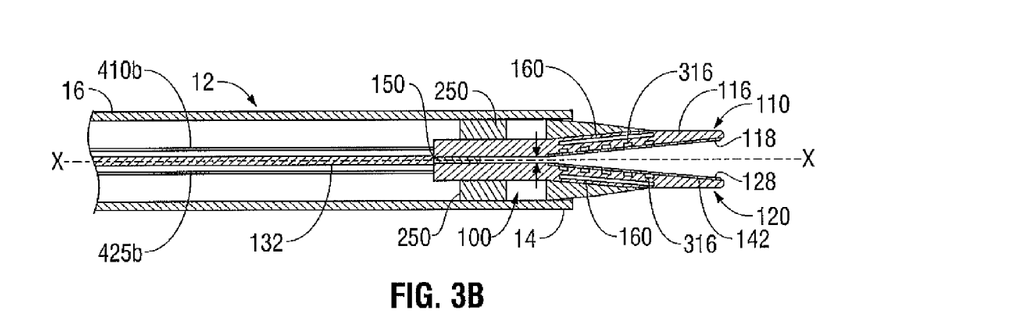
Figure 3C:
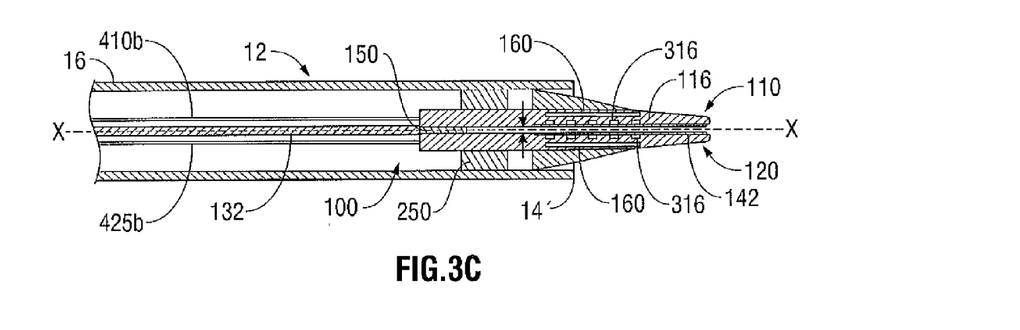
Figure 4:
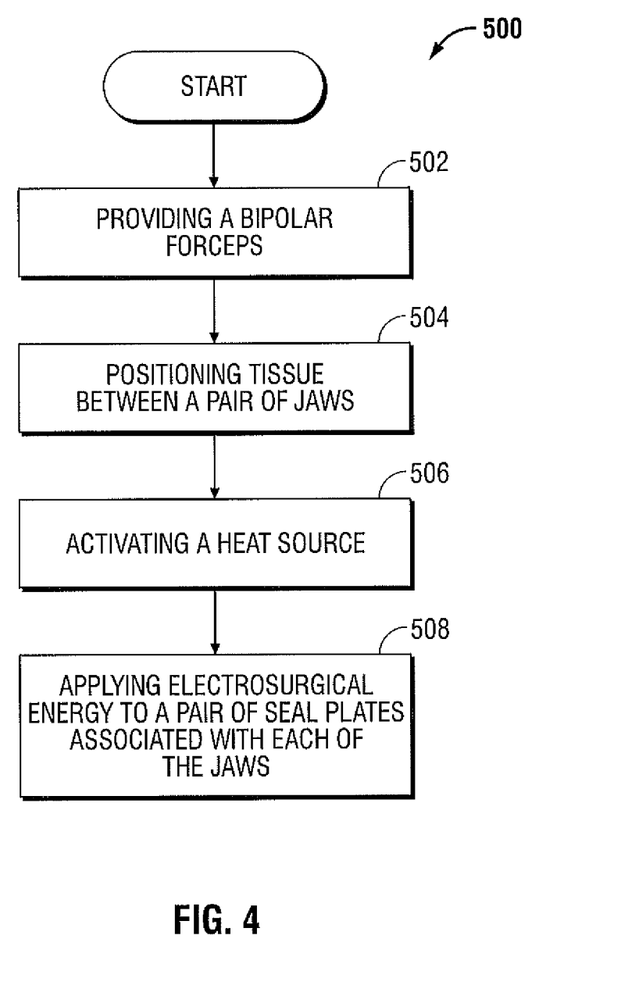
FIG. 4 is a flowchart illustrating a method for performing an electrosurgical procedure in accordance with the present disclosure.

In the embodiments illustrated in FIGS. 3A-3C, each of the jaw members 110, 120 are in electrical communication with one or more cable leads (e.g., 410b, 425b, respectively) of cable 410.

Additionally, each of the jaw members 110, 120 are in electrical communication with one or more heating wires or cables 132 that operatively connects to one or both of the jaw members 110, 120. In the embodiments illustrated in FIGS. 3A-3C, heating cable 132 operatively connects to a heating element or filament 150 (filament 150) that is disposed between jaw members 110, 120. In some embodiments, an insulative substrate (not explicitly shown) may be disposed between the filament 150 and each of the jaw members 110, 120 and/or their respective seal plates 118, 128. The insulative substrate may facilitate in preventing shorts from occurring between the jaw members 110, 120. Filament 150 is configured to heat one or both of the jaw members 110, 120 such that one or both of the jaw members 110, 120 transition from an open position to a closed position. With this purpose in mind, electrosurgical surgical energy is transmitted to filament 150 such that the electrical resistance of the filament 150 generates heat that enables one or both of the jaw members 110, 120 to transition form an open position to a closed position. In other embodiments, filament 150 is in the form of thermoelectric coolers (TEC's).

In the illustrated embodiment, one or both of the jaw members 110, 120, or portions thereof, are made from shape memory alloy (SMA) also referred to in the art as smart alloy, memory metal, and muscle wire. In some embodiments, seal plates 118, 128 are each made from shape memory alloy. Shape memory alloy suitable for use with the jaw members 110, 120 may include by are not limited to copper-zinc-aluminum-nickel, copper-aluminum-nickel, and nickel-titanium (NiTi), commonly referred to in the art as Nitinol) alloys. In some embodiments, the SMA may be configured for one-way or two-way shape memory effect. Each of the seal plates 118, 128 may include a non-stick surface 142 such as, for example, a wire mesh made from PTFE that facilitates tissue from sticking to the seal surfaces of the seal plates 118, 128.

Operation of bipolar forceps 10 is now described. For illustrative purposes, operation of forceps 10 is described in terms of an SMA that is configured for two-way shape memory effect. In this instance, the SMA associated with each of the sealing plates 118, 128 of jaw members 110, 128, respectively, remembers two different shapes, a "cold" shape (e.g., jaw members are in an open position) and a "hot" shape (e.g., jaw members are in a closed position). For purposes herein, $M_f$ is the temperature at which the transition to a martensite phase or stage is finished during cooling, and $A_s$ and $A_f$ are the temperatures at which the transition from the martensite phase to austenite phase starts and finishes, during heating. $A_s$ may be determined by the SMA material and composition and, typically, ranges from about −150° C. to about 200° C. $A_f$ may also be determined by the SMA material and composition and/or the loading conditions and, typically, ranges from about 2° C. to about 20° C. or hotter.

The jaw members 110, 120 initially may be in an open position. This open position is a result of the SMA associated with the seal plates 118, 128 being in a cold state, that is, the SMA is in a martensite state (e.g., $M_f$ a point below $A_s$). A user positions tissue between the jaw members 110, 120. A user may then activate the generator 200, for example, by way of switch 60 which may instruct one or more modules (e.g., a control module) to transmit electrosurgical energy to the heating filament 150 via heating cable 132. As heating element 150 "heats up" it causes the seal plates 118, 128 to "heat up" as well. As the seal plates 118, 128 reach an austenite state (e.g., $A_s$) they begin to transition from their "cold" shape to their "hot" shape, which, in turn, causes the jaw members 110, 120 to move, i.e., bend or flex, toward one another. During the austenite phase transition (e.g., $A_s \rightarrow A_f$), the jaw members 110, 120 continue to move toward one another until the jaw members 110, 120 reach a threshold or final austenite stage ($A_f$). At this stage of the austenite phase, the jaw members are capable of grasping tissue such that a desired tissue effect may be achieved. Once tissue is securely and properly grasped between the jaw members 110, 120, electrosurgical energy may be transmitted to one or both of the seal plates 118, 128 of the jaw members 110, 118, respectively to cause a tissue effect therebetween. As the temperature of the seal plates 118,128 cools, the SMA associated with each of the seal plates 118, 128 transitions from the austenite stage back to the martensite stage such that the jaw members 110, 120 and/or seal plates 118, 128 are caused to return to their initial open positions.

From the foregoing and with reference to the various figure drawings, those skilled in the art will appreciate that certain modifications can also be made to the present disclosure without departing from the scope of the same. For example, a knife or cutter blade configured to divide tissue after a desired tissue effect (e.g., tissue seal) has been achieved may be operatively disposed at the distal end of the end effector assembly 100 and in operative communication therewith.

It is contemplated that each of the jaw members 110, 120 may include one or more channels 160 (FIG. 3A) that operatively couples to a fluid source 500 (via a fluid tube 502, see FIG. 1 for example), which may be in operative communication with the generator 200 and/or system 300 and configured to circulate a suitable fluid (e.g., saline or other suitable fluid) therethrough. As described herein, fluid may be defined as a gas, liquid, or combination thereof. More particularly, the fluid source 500 may circulate chilled saline to the channels 160 operatively disposed on one or both of the jaw members 110, 120. In this instance, the chilled saline is intended reduce or "bring down" the temperature of one or both of the seal plates 118, 128 of jaw members 110, 120, respectively, after the seal plates 118, 128 have reached the $A_f$ phase.

It is contemplated that system 300 may include a module (e.g., fluid control module) that is configured to regulate the fluid source. For example, the control module and/or fluid control module may control the amount, rate, and/or temperature of fluid flow provided by the fluid source 500.

It is further contemplated that a sensor module senses electromagnetic, electrical, and/or physical parameters or properties at the operating site and communicates with the control module and/or fluid control module. The sensor module may be configured to measure, i.e., "sense", various electromagnetic, electrical, physical, and/or electromechanical conditions, such as at or proximate the operating site, including: tissue impedance, tissue and/or seal plate 118, 128 temperature, pressure, etc. For example, sensors of the sensor module may include sensors 316 (see FIG. 3A for example) and/or other suitable sensors (e.g., optical sensor(s), proximity sensor(s), etc). The sensor module measures one or more of these conditions continuously or in real-time such that the control module 304 can continually modulate the electrosurgical output and/or control the vacuum source 500.

It is envisioned that in some embodiments, one or more of the sensors (e.g., sensors 316) may include a smart sensor assembly (e.g., a smart sensor, smart circuit, computer, and/or feedback loop, etc. (not explicitly shown)). For example, the smart sensor may include a feedback loop which indicates when a tissue seal is complete based upon one or more of the following parameters: tissue and/or seal surface temperature, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal.

FIG. 5 shows a method 500 for performing an electrosurgical procedure. At step 502, an electrosurgical apparatus including a pair of jaw members configured to grasp tissue therebetween is provided. At step 504, tissue is positioned between the jaw members. At step 506, the electrosurgical energy source is activated causing the first and second jaw members to move towards each other such that tissue is grasped therebetween. And at step 508, electrosurgical energy is applied to the jaw members such that a desired tissue seal may be effected therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps adapted to connect to an electrosurgical energy source for performing an electrosurgical procedure, comprising:

a housing having a shaft that extends therefrom that defines a longitudinal axis therethrough; and an end effector assembly operatively connected to a distal end of the shaft having a pair of first and second jaw members, each of the jaw members having a seal plate disposed on an inner surface thereof, and at least one jaw member being partially manufactured from a shape memory alloy (SMA), the seal plates configured to communicate with a heat source via a heating cable extending the length of the shaft, the heat source configured to heat each of the seal plates, such that the at least one jaw member moves relative to the other from a normally open configuration to a closed configuration for grasping tissue therebetween upon transition of the SMA from a martensite phase to an austenite phase as a result of selectively supplying heat from the heat source thereto.

2. The electrosurgical forceps according to claim 1, wherein at least one of the first and second jaw members includes a non-stick material.

3. The electrosurgical forceps according to claim 1, wherein the heat source is a thermoelectric cooler.

4. The electrosurgical forceps according to claim 1, wherein each of the jaw members includes an insulative housing.

5. The electrosurgical forceps according to claim 4, wherein the insulative housing is malleable and configured to bend upon application of heat to the jaw members.

6. The electrosurgical forceps according to claim 1, wherein at least one sensor is operatively coupled to at least one of the first and second jaw members and in operative communication with the source of electrosurgical energy for controlling electrosurgical energy to the end effector assembly.

7. The electrosurgical forceps according to claim 1, wherein the SMA is selected from the group consisting of copper-zinc-aluminum-nickel, copper-aluminum-nickel, and nickel-titanium.

8. A method for performing an electrosurgical procedure, the method comprising:

providing a bipolar forceps including:

a housing having a shaft that extends therefrom that defines a longitudinal axis therethrough; and an end effector assembly operatively connected to a distal end of the shaft having a pair of first and second jaw members, each of the jaw members having a seal plate disposed on an inner surface thereof, at least one jaw member being partially manufactured from a shape memory alloy (SMA), the seal plates configured to communicate with a heat source via a heating cable extending the length of the shaft, the heat source configured to heat each of the seal plates;

positioning tissue between the pair of first and second jaw members;

activating the heat source to cause at least one of the jaw members to move towards the other such that the tissue is grasped therebetween upon transition of the SMA from a martensite phase to an austenite phase; and applying electrosurgical energy to the jaw members such that the tissue may be treated therebetween.

9. The method according to claim 8, further comprising providing each of the first and second jaw members with a non-stick material.

* * * * *